United States Patent
Parnham et al.

(10) Patent No.: US 11,553,977 B2
(45) Date of Patent: Jan. 17, 2023

(54) HYSTEROSCOPY SYSTEMS AND METHODS FOR MANAGING PATIENT FLUID

(71) Applicant: Covidien LP, Mansfield, MA (US)

(72) Inventors: Linda T. Parnham, Hollis, NH (US); Lisa M. Quealy, Dracut, MA (US); Jonathan M. Bannon, Blackstone, MA (US)

(73) Assignee: COVIDIEN LP, Mansfield, MA (US)

( * ) Notice: Subject to any disclaimer, the term of this patent is extended or adjusted under 35 U.S.C. 154(b) by 195 days.

(21) Appl. No.: 16/880,150

(22) Filed: May 21, 2020

(65) Prior Publication Data

US 2020/0375685 A1 Dec. 3, 2020

Related U.S. Application Data

(60) Provisional application No. 62/854,205, filed on May 29, 2019.

(51) Int. Cl.
*A61B 50/13* (2016.01)
*A61B 1/00* (2006.01)
(Continued)

(52) U.S. Cl.
CPC .......... *A61B 50/13* (2016.02); *A61B 1/00045* (2013.01); *A61B 1/00119* (2013.01); *A61B 1/00147* (2013.01); *A61B 1/015* (2013.01); *A61B 17/320783* (2013.01); *A61B 34/35* (2016.02)

(58) Field of Classification Search
CPC ................ A61M 3/022; A61M 1/0058; A61M 2205/3393; A61M 2205/50; A61M 1/777; A61M 3/0229; A61M 1/77; A61M 2205/125; A61M 2205/126; A61M 1/60; A61M 1/0023; A61M 1/80; A61M 1/0001; A61M 1/71
See application file for complete search history.

(56) References Cited

U.S. PATENT DOCUMENTS 1,585,934 A 5/1926 Muir
1,666,332 A 4/1928 Hirsch
(Continued)

FOREIGN PATENT DOCUMENTS

DE 3206381 A1 9/1983
DE 3339322 A1 5/1984
(Continued)

OTHER PUBLICATIONS

International Search Report and Written Opinion for application No. PCT/US2020/033954 dated Jul. 24, 2020.

*Primary Examiner* — Alexandra L Newton
(74) *Attorney, Agent, or Firm* — Carter, DeLuca & Farrell LLP

(57) ABSTRACT

A low profile surgical system includes a movable cart assembly, an endoscope, and a surgical instrument. The movable cart assembly includes a fluid source and a receptacle assembly that are in fluid communication with one another. The endoscope is operably coupled to the cart assembly and in fluid communication with the fluid source. The surgical instrument is operably coupled to the cart assembly. The surgical instrument and the endoscope are configured to dispense outflow fluid into the receptacle assembly.

19 Claims, 2 Drawing Sheets

(51) Int. Cl.
*A61B 1/015* (2006.01)
*A61B 34/35* (2016.01)
*A61B 17/3207* (2006.01)

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,460,490 A | 10/1995 | Carr et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |

(56) References Cited

U.S. PATENT DOCUMENTS

| | | |
|---|---|---|
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,117,127 A * | 9/2000 | Helmreich ............ A61B 50/10 606/1 |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,224,617 B1 | 5/2001 | Saadat et al. |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,597,662 B2 | 10/2009 | Litscher et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,828,023 B2 | 9/2014 | Neff et al. |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 9,943,639 B2 * | 4/2018 | Germain ............ A61M 3/0212 |
| 2001/0039963 A1 | 11/2001 | Spear |
| 2001/0047183 A1 | 11/2001 | Privitera |
| 2002/0058859 A1 | 5/2002 | Brommersma |
| 2002/0165427 A1 | 11/2002 | Yachia |
| 2003/0050603 A1 | 3/2003 | Todd |
| 2003/0050638 A1 | 3/2003 | Yachia |
| 2003/0078609 A1 | 4/2003 | Finlay |
| 2003/0114875 A1 | 6/2003 | Sjostrom |
| 2003/0138349 A1* | 7/2003 | Robinson ............ A61M 1/342 604/4.01 |
| 2004/0204671 A1 | 10/2004 | Stubbs |
| 2005/0043690 A1 | 2/2005 | Todd |
| 2005/0085692 A1 | 4/2005 | Kiehn |
| 2006/0036132 A1 | 2/2006 | Renner |
| 2006/0047185 A1 | 3/2006 | Shener |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams |
| 2008/0097469 A1 | 4/2008 | Gruber |
| 2008/0097470 A1 | 4/2008 | Gruber |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2009/0082628 A1 | 3/2009 | Kucklick |
| 2009/0270812 A1 | 10/2009 | Litscher |
| 2009/0270895 A1 | 10/2009 | Churchill |
| 2009/0270896 A1 | 10/2009 | Sullivan |
| 2009/0270897 A1 | 10/2009 | Adams |
| 2009/0270898 A1 | 10/2009 | Chin |
| 2010/0087798 A1 | 4/2010 | Adams |
| 2010/0152647 A1 | 6/2010 | Shener |
| 2011/0034943 A1 | 2/2011 | Churchill |
| 2011/0077674 A1 | 3/2011 | Sullivan et al. |
| 2011/0118544 A1 | 5/2011 | Adams |
| 2011/0166419 A1 | 7/2011 | Reif |
| 2012/0067352 A1 | 3/2012 | Gruber |
| 2012/0078038 A1 | 3/2012 | Sahney |
| 2012/0165642 A1* | 6/2012 | Krensky ............... A61M 1/60 600/371 |
| 2013/0131452 A1 | 5/2013 | Kuroda |
| 2014/0031834 A1 | 1/2014 | Germain |
| 2016/0220971 A1 | 8/2016 | Volker |
| 2017/0172796 A1 | 6/2017 | Biancalana et al. |
| 2018/0361055 A1* | 12/2018 | Pereira ............... A61M 3/022 |

(56) References Cited

U.S. PATENT DOCUMENTS

| | | | |
|---|---|---|---|
| 2019/0008371 | A1 | 1/2019 | Shener-Irmakoglu et al. |
| 2020/0297900 | A1* | 9/2020 | Holigan ................ A61M 1/777 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 1050834 A | 10/1963 |
| GB | 2093353 A | 9/1982 |
| GB | 2311468 A | 10/1997 |
| JP | 2001075416 A | 3/2001 |
| JP | 2002045842 A | 2/2002 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |
| WO | 2016025132 A1 | 2/2016 |

\* cited by examiner

HYSTEROSCOPY SYSTEMS AND METHODS FOR MANAGING PATIENT FLUID

CROSS REFERENCE TO RELATED APPLICATIONS

This application claims the benefit of U.S. Provisional Application Ser. No. 62/854,205, filed May 29, 2019, the entire contents of which are incorporated by reference herein.

TECHNICAL FIELD

This disclosure relates to surgical systems and methods for managing patient fluid, and more particularly, for managing patient fluid during a hysteroscopy procedures.

BACKGROUND

Surgical procedures, such as tissue resection procedures, may be performed endoscopically within an organ, such as a uterus, by inserting an endoscope into the uterus and passing a tissue resection device through the endoscope and into the uterus. With respect to such endoscopic tissue resection procedures, it often is desirable to distend the uterus with fluid provided from a fluid bag, or other fluid source. This fluid may include, for example, saline, sorbitol, or glycine. The inflow and outflow of fluid during the procedure maintains the uterus in a distended state and flushes tissue and other debris from within the uterus to maintain a visible working space.

SUMMARY

The disclosure generally relates to a surgical cart system that facilitates intra-uterine tissue resection and management of fluid during such procedures. Advantageously, the surgical cart system has a low-profile arrangement that can be positioned underneath a patient's bed to effectuate a procedure and rolled out of the way, for example, into a corner when not in use. The surgical cart system also advantageously provides shortened tubing profiles that can be maintained in front of the clinician during a procedure without cumbersome set up or unduly encumbering space within an operating theater.

In aspects of the disclosure, a surgical cart system includes a cart assembly, an endoscope, a fluid source, and a receptacle assembly. The cart assembly includes one or more wheels configured to facilitate transport. The endoscope is operably coupled to the cart assembly. The fluid source is operably supported on cart assembly and in fluid communication with the endoscope. The fluid source is configured to deliver inflow fluid to a patient positioned on a bed of the patient. The receptacle assembly is operably supported on the cart assembly and configured to receive outflow fluid. The surgical cart system includes a profile configured to enable the cart and receptacle assemblies to be positioned beneath the patient's bed when the endoscope is utilized to effectuate a surgical procedure on the patient.

In embodiments, the cart assembly may include an inflow scale and an outflow scale. The inflow and outflow scales may be configured to monitor fluid deficit in the surgical cart system.

In various embodiments, the surgical cart system may further include a pressure pump operably supported on the cart assembly and positioned to pressurize the fluid source.

In embodiments, the surgical cart system may further include a display assembly operably supported on the cart assembly. The display assembly may be electrically coupled to a controller assembly and may be configured to control information displayed on the display assembly. The display assembly may be rotatably coupled to the cart assembly to enable the display assembly to swivel relative to the cart assembly. The display assembly may be a touch-screen display configured to receive input and electrically communicate the input to the controller assembly.

In various embodiments, the surgical cart system may further include a surgical instrument operably supported on the cart assembly and in fluid communication with the receptacle assembly. The surgical instrument may be a tissue resecting instrument.

In embodiments, the receptacle assembly may include a receptacle bag and a container operably supported on the cart assembly. The receptacle bag may be in fluid communication with the container. The receptacle bag may support a trap configured to trap debris or tissue received in the receptacle bag while enabling fluid to pass through the trap so that the fluid can collect in a bottom of the receptacle bag.

According to one aspect, this disclosure is directed to a low profile surgical system. The low profile surgical system includes a movable cart assembly, an endoscope, and a surgical instrument. The movable cart assembly includes a fluid source and a receptacle assembly that are in fluid communication with one another. The endoscope is operably coupled to the cart assembly and in fluid communication with the fluid source. The surgical instrument is operably coupled to the cart assembly. The surgical instrument and the endoscope are configured to dispense outflow fluid into the receptacle assembly.

In embodiments, the cart assembly may include an inflow scale and an outflow scale, the inflow and outflow scales configured to monitor fluid deficit in the low profile surgical system.

In some embodiments, the cart assembly may include a pressure pump configured to pressurize the fluid source.

The cart assembly may include a display assembly and a controller assembly that are electrically coupled together to display information on the display assembly. The display assembly may swivel relative to the cart assembly. The display assembly may be a touch-screen display.

The receptacle assembly may include a receptacle bag and a container operably supported on the cart assembly. The receptacle bag may be in fluid communication with the container by a tube. The receptacle bag may support a trap configured to trap debris or tissue received in the receptacle bag while enabling fluid to pass through the trap so that the fluid collects in a bottom of the receptacle bag and feeds into the container by the tube.

According to yet another aspect, this disclosure is direct to a method for managing fluid during a surgical procedure. The method includes dispensing inflow fluid from a fluid source into one or more surgical instruments. The fluid source is supported on a movable cart assembly. The method also involves receiving outflow fluid from the one or more surgical instruments in a receptacle assembly supported on the movable cart assembly while the receptacle assembly and the movable cart assembly are positioned beneath a patient's bed.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
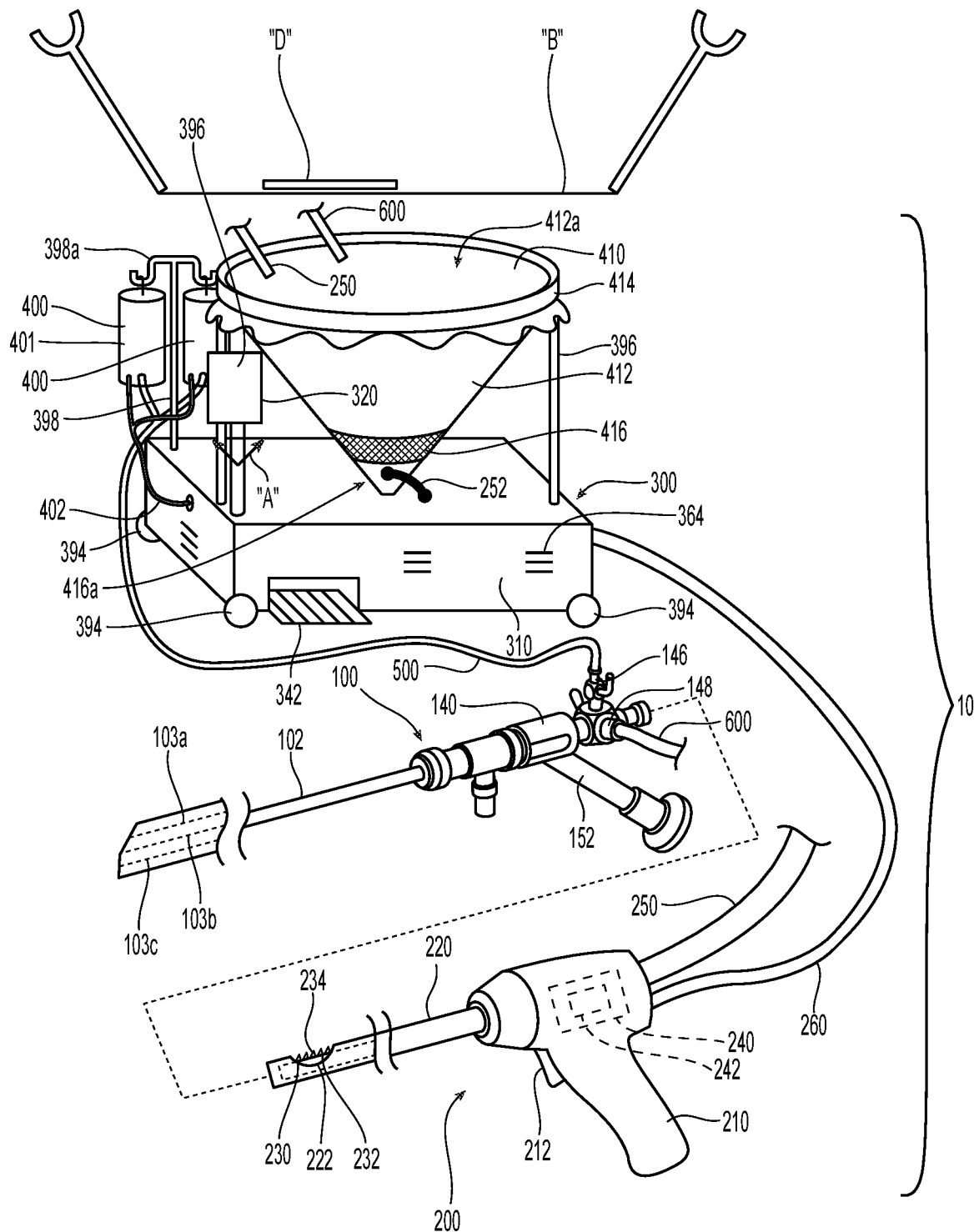
FIG. 1 is a perspective view of a surgical cart system positioned beneath a patient's bed in accordance with the principles of this disclosure.

Embodiments of this disclosure are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. Additionally, the term "proximal" refers to the portion of structure that is closer to the clinician and the term "distal" refers to the portion of structure that is farther from the clinician. In the following description, well-known functions or constructions are not described in detail to avoid obscuring this disclosure in unnecessary detail.

Referring to FIG. 1, a surgical cart system exemplifying the aspects and features of this disclosure is shown generally identified by reference numeral 10. Surgical cart system 10, which may be a hysteroscopy cart system, generally includes an endoscope 100, a surgical instrument 200, and a cart assembly 300 that has a low-profile configuration suitable for positioning underneath a patient's bed "B" (e.g., below a bed height thereof). Cart assembly 300 supports one or more fluid sources 400 that couple to endoscope 100 by an inflow fluid tube 500, a receptacle assembly 410 selectively coupled to cart assembly 300, and a display assembly 320 that may be rotatably mounted to cart assembly 300, as indicated by arrows "A" to facilitate viewing by one or more clinician's in the operating theater. Although detailed herein with respect to surgical cart system 10, the aspects and features of this disclosure are equally applicable for use with other surgical systems.

For the purposes herein, the components of surgical system 10 are generally described.

Endoscope 100 of surgical cart system 10 is detailed herein as a hysteroscope configured for use in gynecological surgical procedures within the uterus of a female patient. However, other suitable endoscopes and fluid-delivery devices are also contemplated. Endoscope 100 includes an elongated tubular member 102 and a proximal body 140. Proximal body 140 includes an inflow valve 146, an outflow valve 148, and an arm 152 that is configured to connect to an imaging device (e.g., a camera) to capture images received via a visualization mechanism, e.g., optics (not shown), extending through elongated tubular member 102.

Elongated tubular member 102 of endoscope 100 defines a first channel 103a for fluid inflow, a second channel 103b that is shared between fluid outflow and instrument access, e.g., for instrument 200, and a third channel 103c housing optics (not shown). First channel 103a is coupled to inflow valve 146 to enable the introduction of fluid through first channel 103a of endoscope 100 and into a patient, e.g., into the patient's uterus. Fluid inflow fluid tube 500 of fluid source 400 is coupled to inflow valve 146 for enabling the delivery of fluid from fluid source 400 to endoscope 100 and, thus, from fluid source 400 into the patient. Second channel 103b is coupled to outflow valve 148 via an outflow fluid tube 600 to enable the withdrawal of fluid from the patient through endoscope 100 and outflow fluid tube 600, e.g., for depositing into receptacle assembly 410 and, ultimately, into one or more collection containers 325 of receptacle assembly 410 via vacuum tubing 252.

Continuing with reference to FIG. 1, surgical instrument 200 is detailed herein as a tissue resecting instrument; however, other suitable surgical instruments are also contemplated. Surgical instrument 200 generally includes a housing 210, a shaft 220, a cutting member 230, a drive mechanism 240, an outflow tissue and fluid tubing 250, and a cable 260. Housing 210 supports drive mechanism 240 therein and functions as a handle to enable a user to grasp and manipulate surgical instrument 200. Housing 210 may include an actuator 212 disposed thereon for selectively activating surgical instrument 200.

Shaft 220 extends distally from housing 210 and, in embodiments, is stationary relative to housing 210, although other configurations are also contemplated. Shaft 220 defines a window 222 through a side wall thereof towards a distal end thereof to provide access to cutting member 230 which is rotatably and/or translatably disposed within shaft 220 and operably coupled to drive mechanism 240, as detailed below. Cutting member 230 defines an opening 232 providing access to the interior thereof and may include a serrated cutting edge 234 surrounding opening 232, although other suitable cutting edge configurations are also contemplated. Alternatively or additionally, shaft 220 may include a cutting edge defined about window 222.

Drive mechanism 240 includes a motor 242 and is operably coupled to cutting member 230 to drive rotation and/or translation of cutting member 230 relative to shaft 220. Drive mechanism 240 is adapted to connect to cart assembly 300 via cable 260 for powering and controlling motor 242. Actuator 212 may be coupled to drive mechanism 240 and/or cart assembly 300 to enable the selective activation of surgical instrument 200, e.g., selective rotation and/or translation of cutting member 230.

Figure 2:
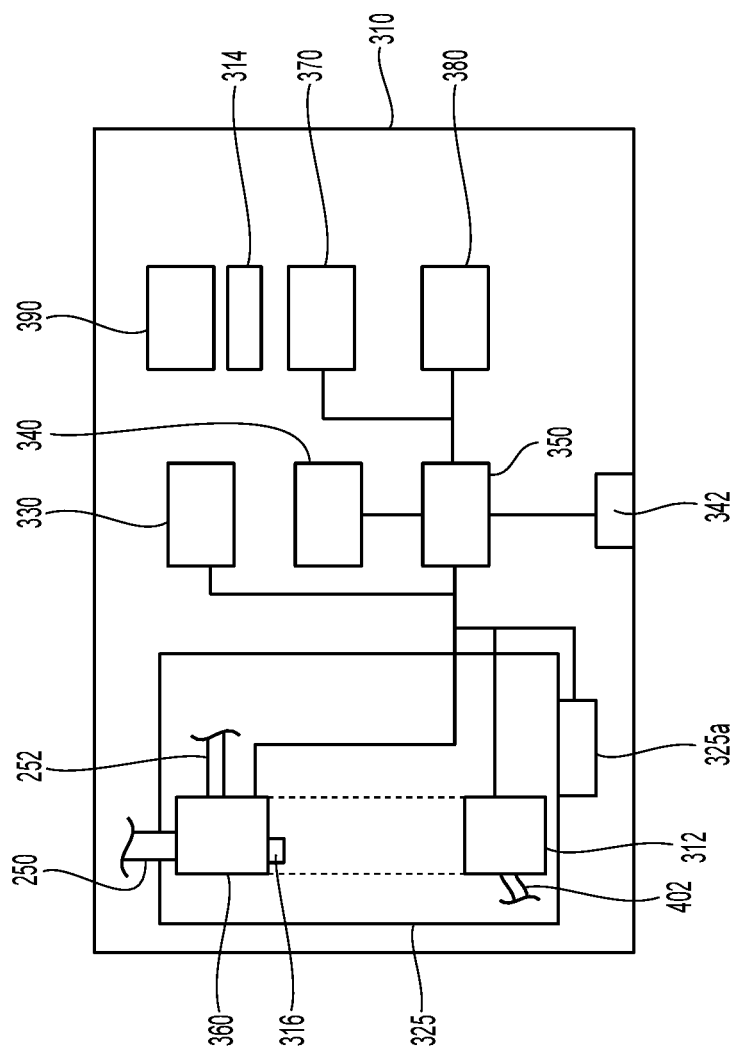
FIG. 2 is a schematic view of a cart assembly of the surgical cart system of FIG. 1.

Outflow tissue and fluid tubing 250 receives the resected tissue as well as fluid and debris suctioned through cutting member 230 when surgical instrument 200 is activated. Outflow tissue and fluid tubing 250 is operably coupled with a vacuum pump assembly 360 (FIG. 2) of cart assembly 300 to enable the suctioning of the resected tissue, fluid, and debris through cutting member 230 and into outflow tissue and fluid tubing 250 for depositing within one or more collection containers 325 coupled with tissue and fluid tubing 250.

With continued reference to FIG. 1, cart assembly 300, as noted above, is configured to power and control motor 242 of drive mechanism 240 of surgical instrument 200 and to provide suction, via vacuum pump assembly 360 (although other suitable suction sources are also contemplated), to suction resected tissue, fluid, and debris through surgical instrument 200 and outflow tissue and fluid tubing 250 for depositing in one or more of the collection containers 325. Cart assembly 300 may additionally or alternatively include communication, identification, and parameter monitoring components, as detailed below.

Cart assembly 300 generally includes an outer housing 310, a display assembly 320 (e.g., touch screen) accessible from the exterior of outer housing 310 and a controller assembly 330 and associated circuitry (e.g., a printed circuit board, conductors, electronic components, etc.) which may be disposed within outer housing 310 and/or integrally formed with display assembly 320. Controller assembly 330 is configured to control the display of information on display 320 and can be configured to sense information input thereto (e.g., touch-screen). Cart assembly 300 further supports a motor control assembly 340 disposed within outer housing 310 and configured to control drive mechanism 240 of surgical instrument 200, a power supply 350 disposed within outer housing 310 and configured to convert power from a main power supply (not shown) into suitable form for powering drive mechanism 240 of surgical instrument 200, and a vacuum pump assembly 360 configured to suction and control the suctioning of resected tissue, fluid, and debris through surgical instrument 200 via outflow tissue and fluid tubing 250. Vacuum pump assembly 360 can also be configured to suction and control the suctioning of tissue, fluid, and debris collected in receptacle assembly 410 via vacuum tubing 252 coupled to receptacle assembly 410. In some embodiments, tubing 252 can deliver fluid from receptacle assembly 410 to container 325 by gravity feed.

Vacuum pump assembly 360 may include any suitable vacuum pump having an exhaust to expel waste air therefrom, which may be expelled from the outer housing 310 via vents 364 and/or directed towards, over/under, around, between, through, etc. some or all of components (e.g., a pump 312, assemblies 320-380, etc.) such that the waste air is utilized to help those components. This repurposing of the waste air eliminates the need for a cooling fan or fans, reduces the number of cooling fans, and/or reduces the required output of the cooling fan(s). In some embodiments, cart assembly 300 supports one or more cooling fans or heat sinks 314. Additionally, and/or alternatively, an exhaust augmenter 316 operably coupled to the exhaust outflow of vacuum pump assembly 360 may be provided to draw in external air, e.g., through vents 364, to supplement the waste air, thereby further facilitating cooling of the various components of cart assembly 300.

Cart assembly 300 may further include an identification (ID) assembly 370 configured to identify a surgical instrument, e.g., surgical instrument 200, coupled thereto, e.g., via RFID. Cart assembly 300 may additionally or alternatively include a fluid monitoring assembly 380 configured to, for example, monitor fluid flow rate, fluid pressure, total fluid volume, fluid impedance, fluid deficit, etc., and provide feedback regarding the same, e.g., suitable alarms and/or disabling of one or more other assemblies.

As can be appreciated in view of the above, the various components of cart assembly 300 include suitable hardware components and may also include one or more processors and associated memories storing software to be executed by the processor(s) to control the hardware components (although one or more centralized processors and/or memories may alternatively be provided). These components, namely the circuitry thereof, generate waste heat which can be dissipated (e.g., by use of the cooling fans/heats sinks 314, vents 364, etc.) so as to maintain circuitry of these components at safe operating temperatures.

Cart assembly 300 further includes an output 390 enabling coupling of cable 260 of surgical instrument 200 to cart assembly 300. Additional or alternative assemblies and/or other components associated with cart assembly 300 may also be provided. For instance, cart assembly 300 can include a footswitch 342 that may be recessed within housing 310 of cart assembly 300 and is operatively connected to surgical instrument 200, controller 350 and/or motor control assembly 340 of cart assembly 300. Cart assembly 300 can include any number of wheels 394 (e.g., casters) that may be lockable to prevent cart assembly 300 from rolling, or unlockable to enable cart assembly 300 to roll, for example, under the patient's bed "B" or out from under the patient's bed "B" to access, remove, repair and/or replace one or more components of surgical cart system 10. Cart assembly 300 can also include receptacle support poles 396 that support receptacle assembly 410 and fluid source support poles 398 that support fluid sources 400 and include an inflow scale 398a configured to measure fluid characteristics (e.g., volume, weight thereof) within fluid sources 400. Cart assembly 300 can also include an outflow scale 325a configured to measure outflow fluid characteristics (e.g., volume or weight of fluid extracted from the patient and received by the receptacle assembly 410 and/or the one or more containers 325, and which can include outflow fluid from endoscope 100, outflow fluid from the surgical instrument 200, and/or outflow fluid from an underbuttocks drape "D"). In particular, the outflow fluid is collectively weighted by outflow scale 325a to determine fluid deficit.

Fluid sources 400 may be, for example, fluid bags 401 containing a fluid, e.g., saline, sorbitol, or glycine, therein. Fluid bag 401 is connected to an input end of fluid inflow tube 500 which, as noted above, is coupled at an output end thereof to inflow valve 146 of endoscope for enabling delivery of fluid from fluid source 400 to endoscope 100. A pressure pump 312 or other suitable pump (not shown) supported by cart assembly 300 communicates with fluid source 400 via a pressure line 402 to pressurize the fluid supplied to endoscope 100. In some embodiments the pressure pump 312 and the vacuum pump assembly 360 may be the same pump or part of the same assembly. In other embodiments, fluid source 400 can deliver fluid to endoscope 100 under gravity pressure.

Receptacle assembly 410 includes a receptacle bag 412 supported on a mounting ring 414 that holds receptacle bag 412 in place. Mounting ring 414 is supported on support poles 396. Receptacle bag 412 has an open end 412a that receives outflow fluid therein, which includes debris, tissue, and fluid (e.g., blood, saline, etc.). Receptacle assembly 410 further includes a trap 416 that seats in receptacle bag 412 to trap debris and/or tissue received in receptacle bag 412. Trap 416 can include any number of holes 416a configured to enable fluids to pass through trap 416, but prevent the debris and/or tissue from passing through trap 416. Trap 416 is configured to seat in the receptacle bag 412 at a position offset from a bottom of receptacle bag 412 to enable fluid to collect beneath trap 416 before being suctioned out through vacuum tubing 252 and into one or more containers 325 of receptacle assembly 410. Receptacle bag 412 may be formed of any suitable material such a polymeric material (e.g., nylon) and which may be translucent and/or transparent to facilitate visualization through receptacle bag 12. In embodiments, receptacle bag 412 may including a conical configuration, which may facilitate support of trap 416 at a position spaced from a bottom of receptacle bag 412.

Securement of any of the components of the disclosed devices may be effectuated using known securement techniques such welding, crimping, gluing, heat-shrinking, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

What is claimed is:

1. A surgical cart system, comprising:
a cart assembly including an outer housing and at least one wheel configured to facilitate transport;
an endoscope operably coupled to the cart assembly;
a fluid source operably supported on the cart assembly and in fluid communication with the endoscope, the fluid source configured to deliver inflow fluid to a patient positioned on a bed of the patient; and
a receptacle assembly operably supported on the cart assembly and configured to receive outflow fluid, the receptacle assembly including a receptacle bag and a container in fluid communication with the receptacle bag, the receptacle bag suspended above the outer housing of the cart assembly and the container supported within the outer housing, wherein the receptacle bag is supported on a mounting ring, the mounting ring supported over the outer housing of the cart assembly by at least one pole extending from the outer housing of the cart assembly,
wherein the surgical cart system includes a profile configured to enable the cart and receptacle assemblies to be positioned beneath the patient's bed when the endoscope is utilized to effectuate a surgical procedure on the patient.

2. The surgical cart system of claim 1, wherein the cart assembly includes an inflow scale and an outflow scale, the inflow and outflow scales configured to monitor fluid deficit in the surgical cart system.

3. The surgical cart system of claim 1, further comprising a pressure pump operably supported on the cart assembly and positioned to pressurize the fluid source.

4. The surgical cart system of claim 1, further comprising a display assembly operably supported on the cart assembly, the display assembly electrically coupled to a controller assembly and configured to control information displayed on the display assembly.

5. The surgical cart system of claim 4, wherein the display assembly is rotatably coupled to the cart assembly to enable the display assembly to swivel relative to the cart assembly.

6. The surgical cart system of claim 4, wherein the display assembly is a touch-screen display configured to receive input and electrically communicate the input to the controller assembly.

7. The surgical cart system of claim 1, further comprising a surgical instrument operably supported on the cart assembly and in fluid communication with the receptacle assembly.

8. The surgical cart system of claim 7, wherein the surgical instrument is a tissue resecting instrument.

9. The surgical cart assembly of claim 1, wherein the receptacle bag supports a trap configured to trap debris or tissue received in the receptacle bag while enabling fluid to pass through the trap so that the fluid can collect in a bottom of the receptacle bag and drain into the container via a tube extending between the container and the receptacle bag.

10. A surgical system, comprising:
a movable cart assembly including a fluid source and a receptacle assembly that are in fluid communication with one another, the receptacle assembly including a receptacle bag and a container in fluid communication with the receptacle bag, the receptacle bag suspended above the movable cart assembly and the container supported within the movable cart assembly, wherein the receptacle bag is supported on a mounting ring, the mounting ring supported by at least one pole extending from the movable cart assembly;
an endoscope operably coupled to the cart assembly and in fluid communication with the fluid source; and
a surgical instrument operably coupled to the cart assembly,
wherein the surgical instrument and the endoscope are configured to dispense outflow fluid into the receptacle assembly.

11. The surgical system of claim 10, wherein the movable cart assembly includes an inflow scale and an outflow scale, the inflow and outflow scales configured to monitor fluid deficit in the low profile surgical system.

12. The surgical system of claim 10, wherein the movable cart assembly includes a pressure pump configured to pressurize the fluid source.

13. The surgical system of claim 10, wherein the movable cart assembly includes a display assembly and a controller assembly that are electrically coupled together to display information on the display assembly.

14. The surgical system of claim 13, wherein the display assembly swivels relative to the movable cart assembly.

15. The surgical system of claim 13, wherein the display assembly is a touch-screen display.

16. The surgical system of claim 10, wherein the surgical instrument is a tissue resecting instrument.

17. The surgical system of claim 10, wherein the receptacle bag supports a trap configured to trap debris or tissue received in the receptacle bag while enabling fluid to pass through the trap so that the fluid collects in a bottom of the receptacle bag and feeds into the container by the tube.

18. The surgical cart system of claim 10, wherein the receptacle bag has a conical configuration.

19. The surgical system of claim 10, wherein the receptacle bag has a conical configuration with an open end portion that tapers to a closed end portion, the closed end portion coupled to a tube that is disposed in fluid communication with the container.

* * * * *